US010820789B2

United States Patent
Ogata et al.

(10) Patent No.: US 10,820,789 B2
(45) Date of Patent: Nov. 3, 2020

(54) ENDOSCOPE SYSTEM AND LIGHT SOURCE CONTROL METHOD

(71) Applicant: Panasonic i-PRO Sensing Solutions Co., Ltd., Fukuoka (JP)

(72) Inventors: Shigeki Ogata, Fukuoka (JP); Yoshitaka Kitaoka, Osaka (JP); Naoto Matsuo, Fukuoka (JP); Haruhiko Kohno, Fukuoka (JP); Kunihiko Hara, Osaka (JP)

(73) Assignee: PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 13 days.

(21) Appl. No.: 15/141,595

(22) Filed: Apr. 28, 2016

(65) Prior Publication Data

US 2016/0317003 A1    Nov. 3, 2016

(30) Foreign Application Priority Data

Apr. 30, 2015 (JP) .................... 2015-093642

(51) Int. Cl.
*A61B 1/04* (2006.01)
*H04N 5/225* (2006.01)
(Continued)

(52) U.S. Cl.
CPC .............. *A61B 1/043* (2013.01); *A61B 1/045* (2013.01); *A61B 1/0638* (2013.01); *G02B 23/2461* (2013.01); *G02B 23/2484* (2013.01); *H04N 5/2256* (2013.01); *H04N 5/2354* (2013.01); *H04N 5/332* (2013.01); *H04N 2005/2255* (2013.01)

(58) Field of Classification Search
CPC ....... A61B 1/043; A61B 1/045; A61B 1/0638; H04N 5/2256; H04N 5/2354; H04N 5/332; H04N 2005/2255; G02B 23/2461; G02B 23/2484
See application file for complete search history.

(56) References Cited

U.S. PATENT DOCUMENTS 8,630,698 B2    1/2014    Fengler et al.
8,767,058 B2    7/2014    Yoshino et al.
(Continued)

FOREIGN PATENT DOCUMENTS

JP    2010-227253 A    10/2010
JP    2014-087661 A1    5/2014
WO    2011/036792 A1    3/2011

*Primary Examiner* — Md N Haque
*Assistant Examiner* — Berteau Joisil
(74) *Attorney, Agent, or Firm* — Seed IP Law Group LLP (57) ABSTRACT

An endoscope system includes a first light source that emits visible light, a second light source that emits non-visible light, an image sensor that generates a first image including a subject through first photoelectric conversion using the visible light and generates a second image including a subject that emits fluorescence emission light due to excitation by the non-visible light through second photoelectric conversion using the non-visible light, and an output device that alternately switches between and outputs the first image and the second image. The second light source starts light emission by a predetermined time before start of the second photoelectric conversion due to driving of the driving circuit.

18 Claims, 9 Drawing Sheets

(51) Int. Cl.
*A61B 1/045* (2006.01)
*G02B 23/24* (2006.01)
*H04N 5/235* (2006.01)
*A61B 1/06* (2006.01)
*H04N 5/33* (2006.01)

(56) References Cited

U.S. PATENT DOCUMENTS

| | | |
|---|---|---|
| 2003/0135092 A1 | 7/2003 | Cline et al. |
| 2005/0143627 A1 | 6/2005 | Cline et al. |
| 2005/0154319 A1 | 7/2005 | Cline et al. |
| 2006/0241496 A1 | 10/2006 | Fengler et al. |
| 2007/0015963 A1 | 1/2007 | Fengler et al. |
| 2010/0069713 A1* | 3/2010 | Endo ............ A61B 1/0005 600/109 |
| 2011/0122301 A1* | 5/2011 | Yamura ........... H04N 5/2256 348/262 |
| 2012/0013773 A1 | 1/2012 | Yoshino et al. |
| 2013/0293534 A1* | 11/2013 | Sato ............. H04N 13/361 345/419 |
| 2014/0194687 A1 | 7/2014 | Fengler et al. |
| 2014/0354788 A1* | 12/2014 | Yano ............. A61B 1/043 348/68 |
| 2016/0012571 A1* | 1/2016 | Yang ............ G09G 3/3406 345/694 |

* cited by examiner

ENDOSCOPE SYSTEM AND LIGHT SOURCE CONTROL METHOD

BACKGROUND OF THE INVENTION

1. Field of the Invention

The present disclosure relates to an endoscope system and a light source control method.

2. Description of the Related Art

An endoscope system in which an observation part is irradiated with normal light and excitation light that are alternately switched, and the observation part irradiated with each light is imaged is known. For example, JP-A-2010-227253 discloses the endoscope system. The endoscope system described in JP-A-2010-227253 captures a reflected light image of an observation part at a timing at which normal light is radiated, and captures a reflected excitation light image of the observation part at a timing at which excitation light is radiated. Further, this endoscope system captures a fluorescent image of the observation part at the same timing as a timing at which the excitation light is radiated and reflected excitation light is imaged.

In an endoscope system of the related art, image quality of a fluorescent image (fluorescence emission light image) is insufficient.

SUMMARY OF THE INVENTION

The present disclosure has been made in view of the above circumstances, and provides an endoscope system and a light source control method capable of reducing degradation in image quality of a fluorescence emission light image.

An endoscope system of the present disclosure includes a first light source that emits visible light to a subject; a second light source that emits non-visible light to the subject; a driving circuit that drives the first light source and the second light source; an image sensor that generates a first image including the subject through first photoelectric conversion using the visible light, and generates a second image including the subject that emits fluorescence emission light due to excitation by the non-visible light, through second photoelectric conversion using the non-visible light; and an output device that alternately switches between and outputs the first image and the second image. The second light source starts light emission by a predetermined time before a start of the second photoelectric conversion due to driving of the driving circuit.

According to the present disclosure, it is possible to reduce degradation in the image quality of a fluorescence emission light image.

DETAILED DESCRIPTION OF THE INVENTION

Hereinafter, embodiments will be described in detail with appropriate reference to the accompanying drawings. However, unnecessary description may be omitted. For example, detailed description of known matters or repeated description of substantially the same configurations may be omitted. This is intended to avoid unnecessary redundancy of the following description and to facilitate the understanding of those skilled in the art. The accompanying drawings and the following description are provided to those skilled in the art in order to sufficiently understand the present disclosure, and are not intended to limit the subject matter defined in the claims.

Background of Embodiments of the Present Disclosure

In an endoscope system of the related art, exposure of an image sensor is performed simultaneously with irradiation with light. In the case of visible light, the image sensor is exposed simultaneously with irradiation with light, such that a high definition image can be captured. Meanwhile, in the case of excitation light, an observation part is irradiated with the excitation light, the observation part emits fluorescence emission light, and a delay by a predetermined time occurs until the amount of emitted light reaches a peak. Therefore, in a case in which the image sensor is exposed simultaneously with the irradiation with the excitation light, a received light amount of fluorescence emission light becomes insufficient, and a fluorescence emission image may not be obtained with high definition.

Hereinafter, an endoscope system and a light source control method capable of reducing degradation in image quality of a fluorescence emission light image will be described.

First Embodiment

Configurations

Figure 1:
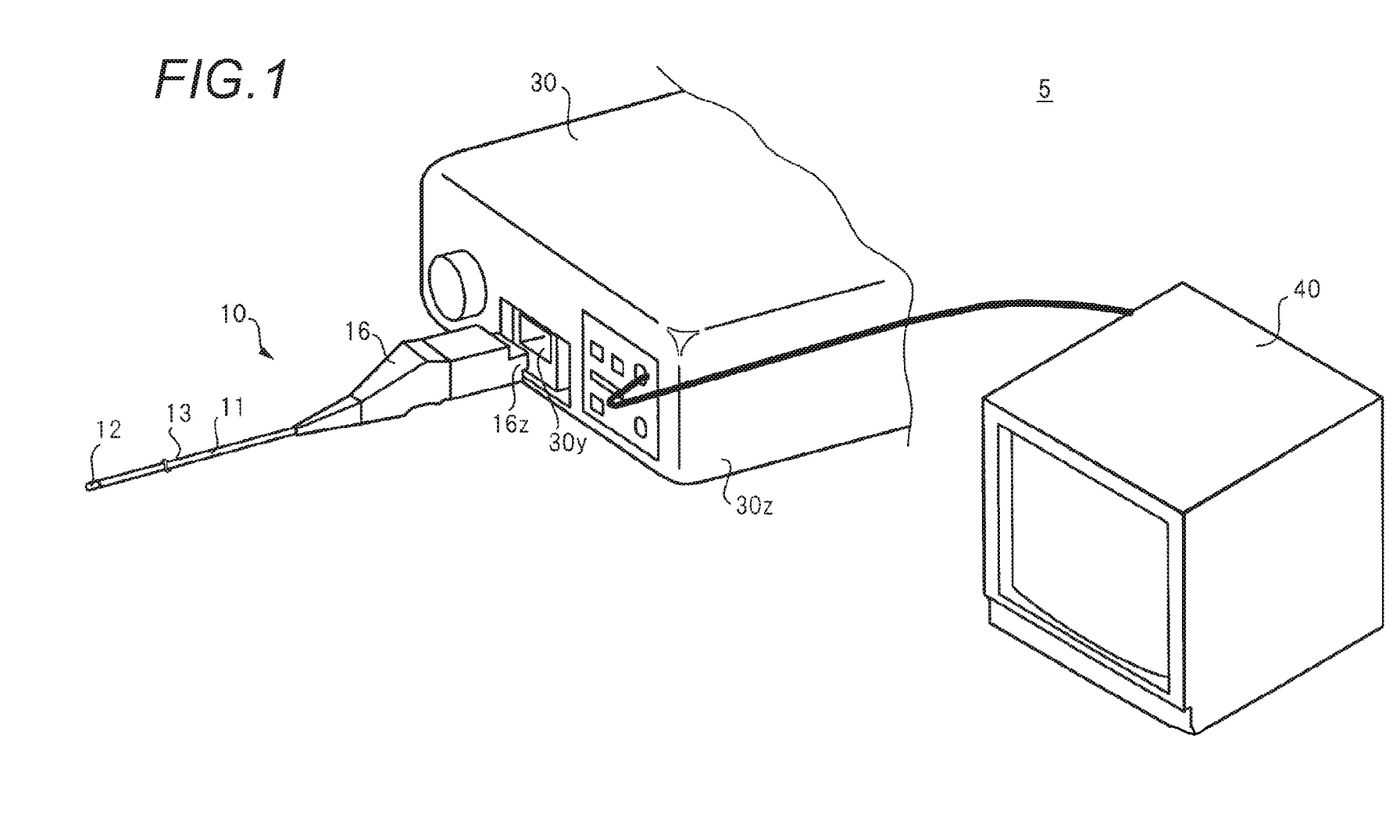
FIG. 1 is a perspective view illustrating an example of an appearance of an endoscope system in an embodiment of the present disclosure.

FIG. 1 is a perspective view illustrating an appearance of an endoscope system 5 in a first embodiment. As terms used herein, an upward direction and a downward direction of a video processor 30 placed on a horizontal plane are referred to as "upper" and "lower", respectively. Further, a side on which an endoscope 10 images an observation target is referred to as "front (tip)", and a side connected to the video processor 30 is referred to as "rear".

The endoscope system 5 includes the endoscope 10, the video processor 30, and a monitor 40. The endoscope 10 is, for example, a medical flexible scope. The video processor 30 performs image processing on a captured image (including a still image and a moving image) obtained by imaging the observation target (here, a human body or the inside of the human body). The monitor 40 displays the image according to a display signal output from the video processor 30. The image processing includes, for example, color correction, gradation correction, and gain adjustment.

The endoscope 10 images the observation target (subject). The endoscope 10 includes a scope 13 inserted into the inside of the observation target, and a plug unit 16 to which a rear end portion of the scope 13 is connected. Further, the scope 13 includes a flexible portion 11 which is relatively long and flexible, and a rigid portion 12 having rigidity provided at a tip of the flexible portion 11. A structure of the scope 13 will be described below.

The video processor 30 includes a housing 30z, performs image processing on the captured image, and outputs a display signal after the image processing. In a front of the housing 30z, a socket unit 30y into which a base end portion 16z of the plug unit 16 is inserted is arranged. The plug unit 16 is inserted into the socket unit 30y and the endoscope 10 is connected to the video processor 30, such that a power and various signals (for example, a video signal and a control signal) can be transmitted and received between the endoscope 10 and the video processor 30. The power and various signals are guided from the plug unit 16 to the flexible portion 11 through a transfer cable (not illustrated) inserted into the inside of the scope 13. Further, an image signal output from an image sensor 22 (solid-state imaging element) (see FIG. 2) provided inside the rigid portion 12 is transferred from the plug unit 16 to the video processor 30 through transfer cable.

The video processor 30 performs image processing on the image signal transferred through the transfer cable, converts image data after the image processing into the display signal, and outputs the display signal to the monitor 40.

The monitor 40 includes, for example, a display device such as a liquid crystal display (LCD) or a cathode ray tube (CRT). The monitor 40 displays the image of the subject captured by the endoscope 10.

Figure 2:
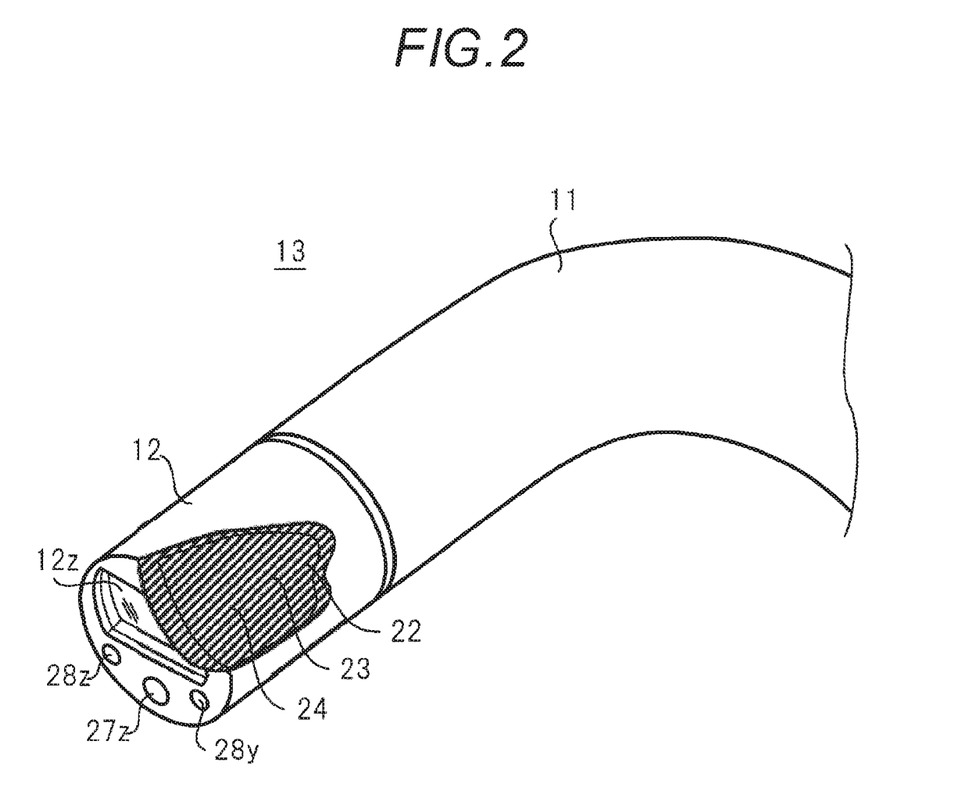
FIG. 2 is a diagram illustrating an example of an internal structure of a rigid portion provided at a tip of a scope in this embodiment.

FIG. 2 is a diagram illustrating an internal structure of the rigid portion 12 provided at the tip of the scope 13. An imaging window 12z is arranged in a tip surface of the rigid portion 12. The imaging window 12z is formed to contain an optical material such as optical glass or optical plastic, and light from the subject is incident on the imaging window 12z.

In the tip surface of the rigid portion 12, an irradiation window 27z to which a tip of an optical fiber 27 that transfers infrared (IR) excitation light from an IR excitation light source 33 (see FIG. 4) is exposed is arranged. In the tip surface of the rigid portion 12, irradiation windows 28z and 28y to which a tip of an optical fiber 28 that transfers visible light from a visible light source 34 (see FIG. 4) is exposed are arranged. Another number of optical fibers 27 and 28 may be provided.

In the inside of the rigid portion 12, a lens 24, an IR excitation light cut filter 23, the image sensor 22, and a first driving circuit 21 (see FIG. 4) are arranged from the imaging window 12z. The number of lenses 24 may be plural. Light (fluorescence emission light or visible light) incident from the imaging window 12z is condensed by the lens 24, transmitted through the IR excitation light cut filter 23, and then, formed as an image on an imaging surface of the image sensor 22.

Figure 3:
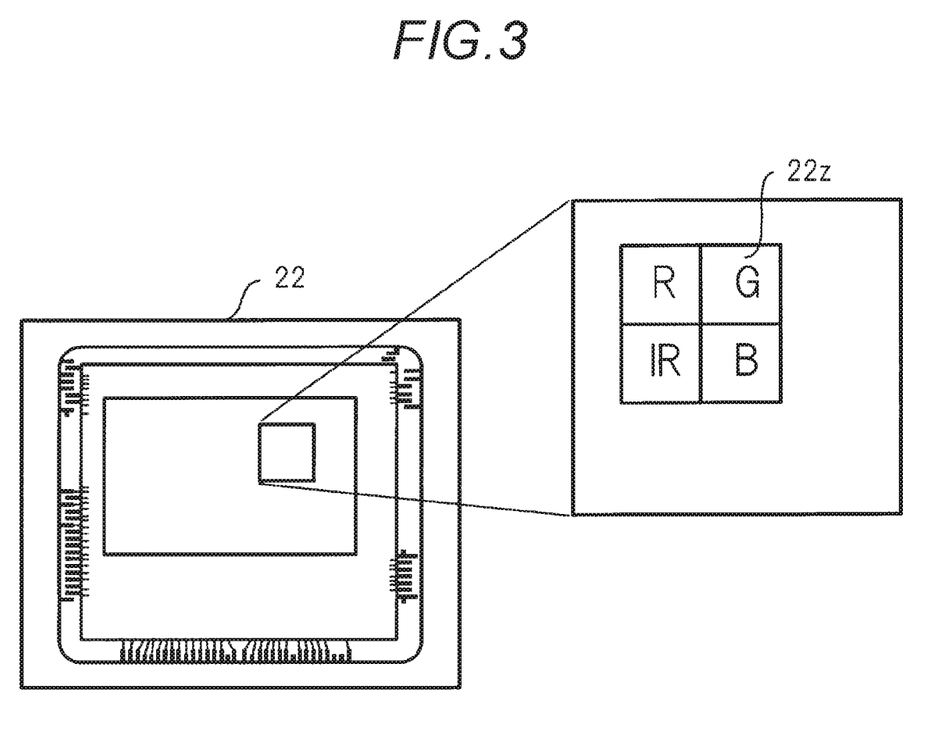
FIG. 3 is a diagram illustrating an example of a structure of an image sensor in this embodiment.

FIG. 3 is a diagram illustrating a structure of the image sensor 22. For the image sensor 22, for example, color filters 22z that transmit infrared light (IR) and light having wavelengths of red (R), blue (B), and green (G) are arranged in a Bayer array in a front of the image sensor 22. The image sensor 22 is, for example, an imaging element having a structure in which a plurality of IR pixels, red pixels, blue pixels, and green pixels that receive light having respective wavelengths are arranged.

The image sensor 22 is, for example, a solid-state imaging element such as a charge coupled device (CCD) or a complementary metal oxide semiconductor (CMOS). The image sensor 22 is used as, for example, a single-plate camera capable of simultaneously receiving infrared light, red light, blue light, and green light.

Figure 4:
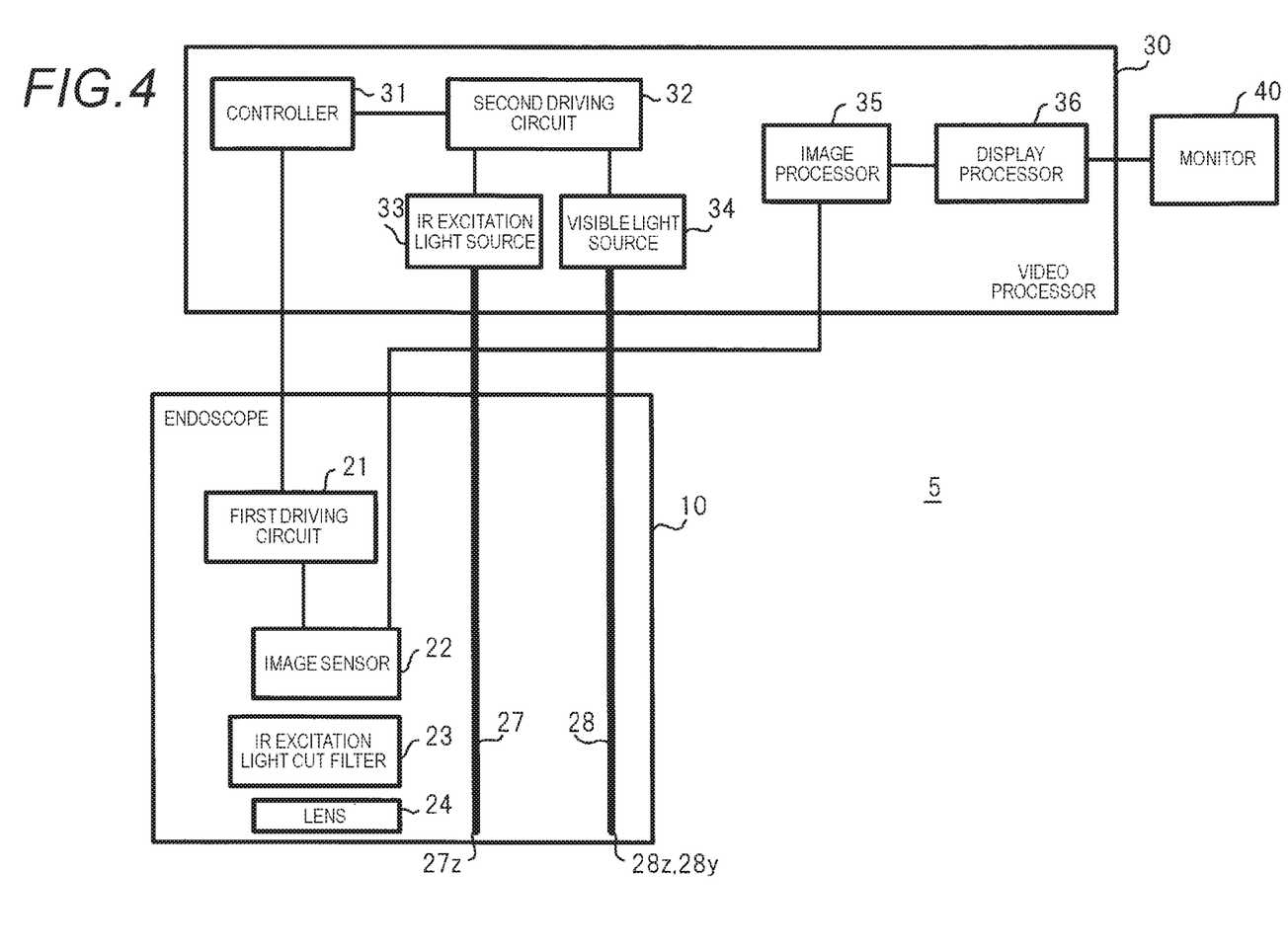
FIG. 4 is a block diagram illustrating an example of a hardware configuration of the endoscope system in this embodiment.

FIG. 4 is a block diagram illustrating a hardware configuration of the endoscope system 5. The endoscope 10 includes the lens 24, the IR excitation light cut filter 23, the image sensor 22, and the first driving circuit 21, which are provided inside the rigid portion 12 of the scope 13, as described above. Further, the endoscope 10 includes the optical fibers 27 and 28 that are inserted into the inside of the scope 13 and extend from the base end portion 16z of the plug unit 16 to the tip surface of the rigid portion 12.

The first driving circuit 21 operates as a driving unit, and turns on and off an electronic shutter of the image sensor 22. In a case in which the electronic shutter is turned on by the first driving circuit 21, the image sensor 22 performs photoelectric conversion on an optical image formed on the imaging surface, and outputs an image signal. In the photoelectric conversion, exposure of the optical image and generation or reading of the image signal are performed.

The IR excitation light cut filter 23 is arranged in front (on light reception side) of the image sensor 22. The IR excitation light cut filter 23 shields the IR excitation light reflected by the subject and transmits fluorescence emission light and visible light caused by the IR excitation light in the light passing through the lens 24. Characteristics of the IR excitation light cut filter 23 will be described below.

The video processor 30 includes a controller 31, a second driving circuit 32, the IR excitation light source 33, the visible light source 34, an image processor 35, and a display processor 36.

The controller 31 generally controls an imaging operation. The controller 31 performs light emission control on the second driving circuit 32, and performs driving control on the first driving circuit 21 of the endoscope 10.

The second driving circuit 32 is, for example, a light source driving circuit, and drives the IR excitation light source 33 to cause the IR excitation light to be continuously emitted. The IR excitation light source 33 continuously lights (continuous lighting) and continuously irradiates the subject with the IR excitation light in an imaging period.

This imaging period indicates a period in which an observation part is imaged by the endoscope 10. The imaging period is, for example, a period from reception by the endoscope system 5 of a user operation of turning ON a switch provided in the video processor 30 or the endoscope 10 to reception of a user operation of turning off the switch.

Further, the second driving circuit 32 may drive the IR excitation light source 33 to cause the IR excitation light to be pulse-emitted. In this case, the IR excitation light source 33 intermittently lights (pulse lighting) and pulse-irradiates the subject with the IR excitation light in the imaging period.

The second driving circuit 32 drives the visible light source 34 to cause visible light (white light) to be pulse-emitted. The visible light source 34 pulse-irradiates the subject with the visible light at a timing of capturing a visible light image in the imaging period.

In general, the fluorescence emission light has weak brightness. On the other hand, the visible light is strong light obtained even with a short pulse.

The image processor 35 performs image processing on a fluorescence emission light image and a visible light image alternately output from the image sensor 22 and outputs image data after the image processing.

For example, in a case in which the luminance of the fluorescence emission light image is lower than the luminance of the visible light image, the image processor 35 as a gain controller performs gain adjustment to increase the gain of the fluorescence emission light image. The image processor 35 may perform the gain adjustment by decreasing the gain of the visible light image instead of increasing the gain of the fluorescence emission light image. Further, the image processor 35 may perform the gain adjustment by increasing the gain of the fluorescence emission light image and decreasing the gain of the visible light image. Further, the image processor 35 may perform the gain adjustment by increasing the gain of the fluorescence emission light image to be higher than that of the visible light image and increasing the gain of the visible light image.

The display processor 36 converts the image data output from the image processor 35 into a display signal such as a national television system committee (NTSC) signal suitable for an image display, and outputs the display signal to the monitor 40.

The monitor 40 displays the fluorescence emission light image and the visible light image, for example, in the same area according to the display signal output from the display processor 36. Accordingly, a user can confirm the observation target while viewing the fluorescence emission light image and the visible light image displayed on the monitor 40.

Figure 5:
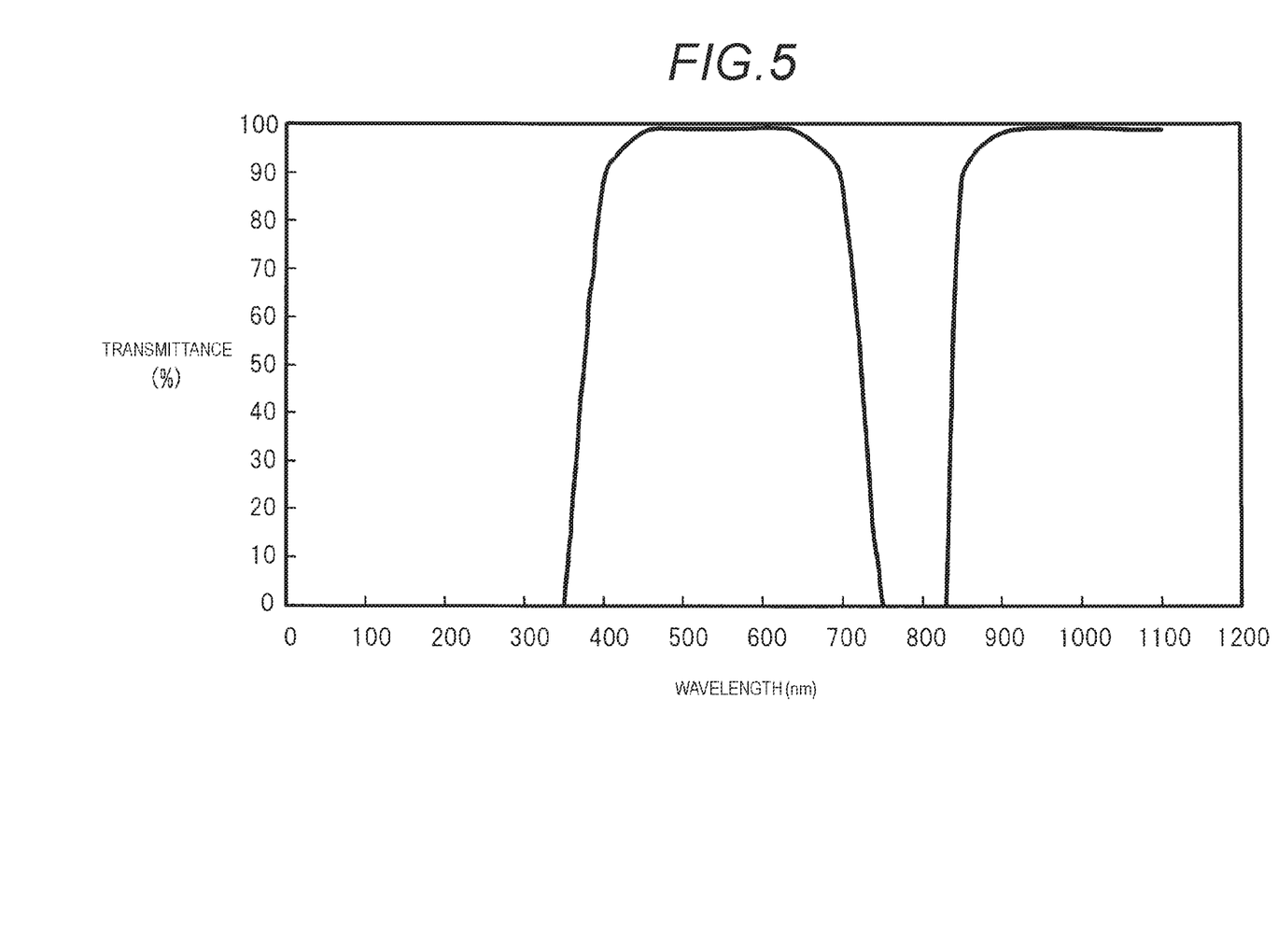
FIG. 5 is a graph illustrating an example of characteristics of an InfraRed (IR) excitation light cut filter in this embodiment.

FIG. 5 is a diagram illustrating characteristics of the IR excitation light cut filter 23. A wavelength of the IR excitation light is, for example, about 780 nm. Further, Indocyamine Green (ICG) that is a fluorescent substance (organic fluorescent dye) is administered into a human body that is an observation target, and the ICG is accumulated in the affected part that is the subject. If the ICG is excited by the IR excitation light, the ICG emits fluorescence emission light having a longer wavelength (about 830 nm).

Generally, IR light (near infrared light) having a wavelength of 700 to 1000 nm is transmitted through skin. Even when the IR light is transmitted through the skin, an influence on a human body is small. Accordingly, the IR light is used for visualization of a structure of a deep part of a living body. For example, ICG is injected into a lymph fluid flowing from a cancer and the flow of the lymph fluid is observed. Accordingly, metastasis of the cancer is easily found. Further, protein is coupled to the ICG such that the cancer is easily collected and a small cancer is easily found.

Further, since the ICG emits fluorescence emission light due to excitation by the IR excitation light, the fluorescence emission light is generated with a delay from the IR excitation light. A delay time thereof is, for example, a few msec, and is different according to a molecular weight of an antibody (protein) coupled to the ICG or according to whether the fluorescence part is a lymph fluid or a blood vessel.

In the IR excitation light cut filter 23 in FIG. 5, transmittance of the fluorescence emission light having a wavelength of about 830 nm is high, and transmittance of the IR excitation light having a wavelength of about 780 nm is substantially 0% and low. Further, for example, transmittance of the visible light having a wavelength of 380 nm to 730 nm is high.

If the IR excitation light is radiated, the IR light is incident through the imaging window 12z provided in a front of the scope 13. The IR excitation light cut filter 23 blocks an optical component in a frequency bandwidth including the IR excitation light (near 780 nm) reflected by the subject in the incident IR light, and transmits an optical component in a frequency band including light of the fluorescence emission (near 830 nm) caused by the IR excitation light.

Accordingly, an optical image by the fluorescence emission is formed on the imaging surface of the image sensor 22. Thus, the IR excitation light cut filter 23 blocks the IR excitation light reflected by the subject, which does not contribute to the fluorescence emission, in the IR excitation light. Further, the visible light is irradiated, and the visible light reflected by the subject, which is incident through the imaging window 12z, is not blocked by the IR excitation light cut filter 23. Therefore, the visible light is formed as the visible light image on the imaging surface of the image sensor 22.

[Operations]

Next, an imaging operation of the endoscope system 5 will be described.

In this embodiment, a case in which the endoscope system 5 performs continuous irradiation with the IR excitation light, and a case in which the endoscope system 5 performs pulse irradiation with the IR excitation light are assumed.

In a case in which a part in a body is imaged using the endoscope 10, indocyanine green (ICG) that is a fluorescent substance is administered into the body, and near-infrared light is applied to an excessively accumulated observation part (affected part) such as a tumor to flash and image the affected part, as described above.

Figure 6:
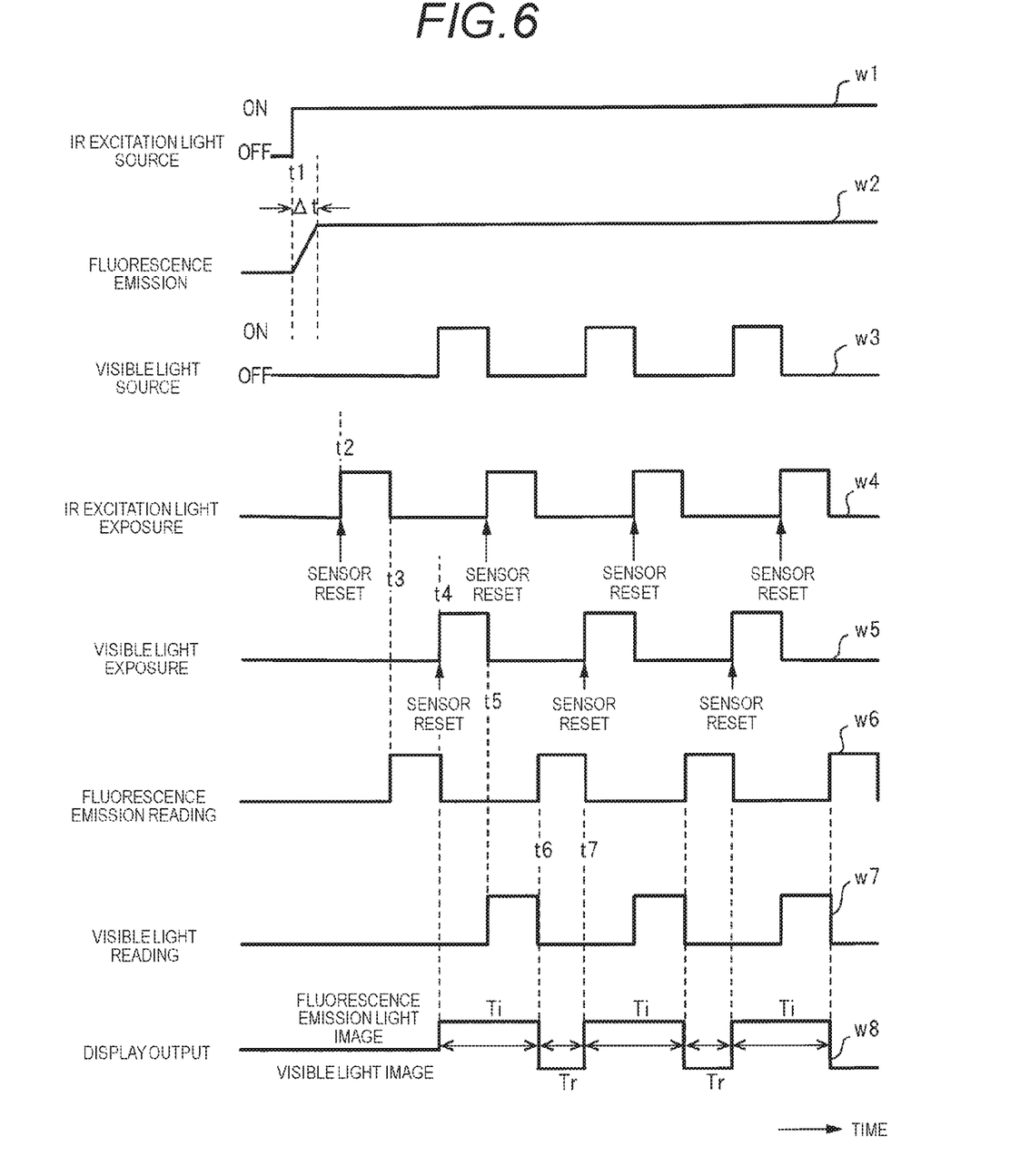
FIG. 6 is a timing chart diagram illustrating an example of an imaging operation of the endoscope system 5 in a case in which continuous irradiation with IR excitation light is performed.
Figure 7:
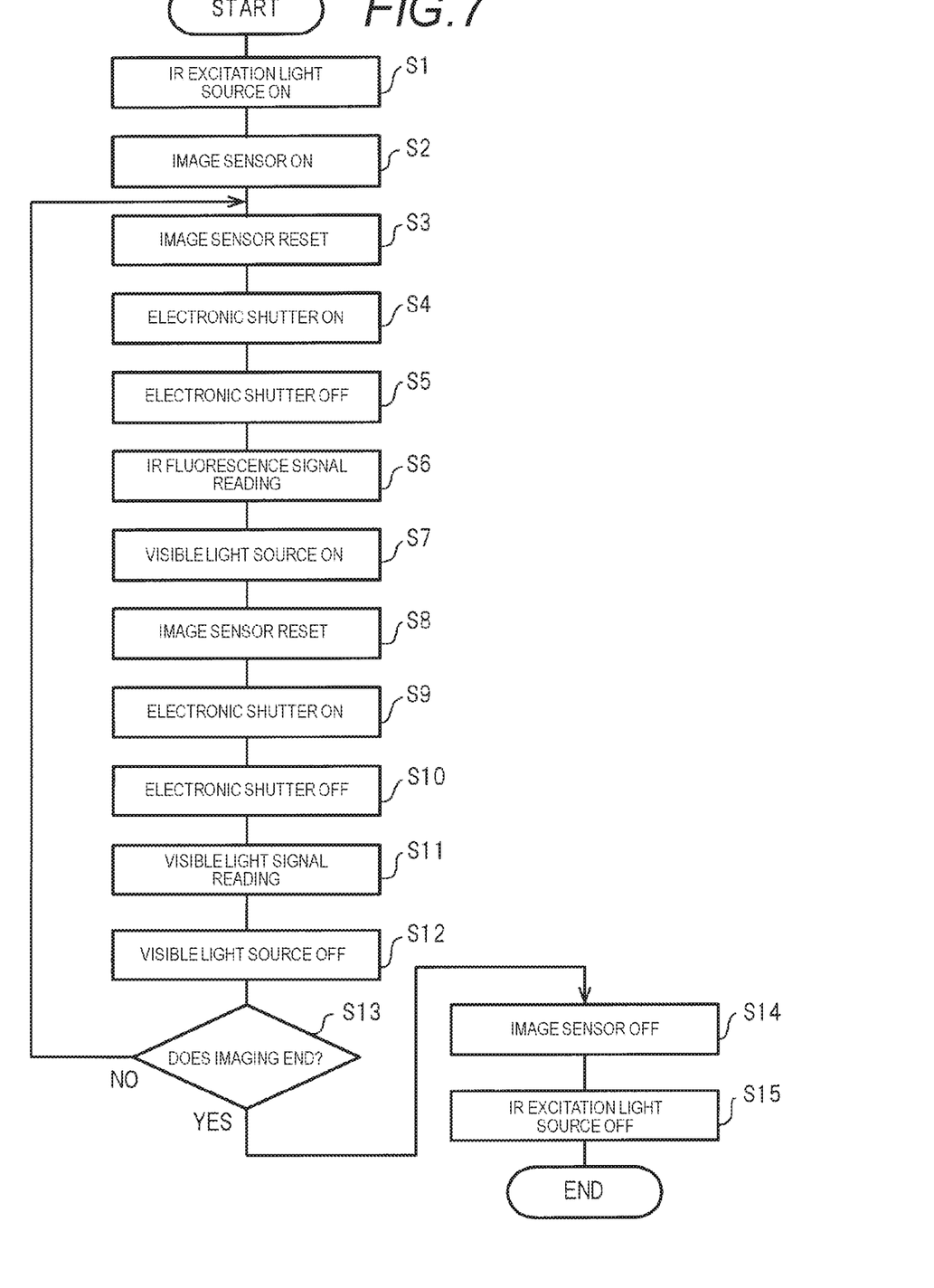
FIG. 7 is a flowchart illustrating an example of an imaging operation procedure of the endoscope system 5 in a case in which continuous irradiation with IR excitation light is performed.

FIG. 6 is a timing chart diagram illustrating an imaging operation of the endoscope system 5 in a case in which continuous irradiation with IR excitation light is performed. FIG. 7 is a flowchart illustrating an imaging operation procedure in the endoscope system 5 in a case in which continuous irradiation with IR excitation light is performed. The endoscope system 5 starts an imaging operation, for example, by receiving an operation of turning on a switch (not illustrated) provided in the video processor 30 or the endoscope 10.

When the imaging operation is started, the controller 31 drives the second driving circuit 32. The second driving circuit 32 turns on the IR excitation light source 33 to cause the IR excitation light to be emitted (S1 in FIG. 7 and a timing t1 in FIG. 6).

When the IR excitation light source 33 emits the IR excitation light, the IR excitation light is radiated from the irradiation window 27z to the subject through the optical fiber 27 in the scope 13, and illuminates a part of the periphery including the affected part. If light from the subject such as the affected part passes through the imaging window 12z, the light is condensed by the lens 24. In the light from the subject such as the affected part, the IR excitation light reflected by the subject is blocked by the IR excitation light cut filter 23, whereas fluorescence emission light from the subject is transmitted through the IR excitation light cut filter 23 to form an image on the imaging surface of the image sensor 22.

In FIGS. 6 and 7, in the imaging period, the IR excitation light source 33 is always turned on (continuously turned on) and the IR excitation light is radiated toward the subject at a certain light amount (a waveform w1 in FIG. 6).

In the subject (affected part) irradiated with the IR excitation light, fluorescence emission light is generated to reach the peak light amount with a delay by a predetermined time Δt (for example, several msec) from the irradiation of the IR excitation light, and the light of the fluorescence emission is output (a waveform w2 in FIG. 6). After the light of the fluorescence emission output from the subject reaches the peak light amount, the irradiation of the IR excitation light is started by a predetermined time Δt or more before exposure start so that the exposure by the fluorescence emission light is started.

The controller 31 outputs a signal for starting the photoelectric conversion of the image sensor 22 to the first driving circuit 21 (image sensor ON) (S2 in FIG. 7). When the first driving circuit 21 receives this signal, the first driving circuit 21 outputs a sensor reset signal to the image sensor 22 to return the image sensor 22 to a state before the start of exposure (sensor resetting) (S3 in FIG. 7 and a timing t2 in FIG. 6). Here, for example, in the case of a CCD image sensor, the first driving circuit 21 clears the charge accumulated by the exposure.

After the sensor is reset, the first driving circuit 21 turns on the electronic shutter of the image sensor 22 to start exposure through fluorescence emission from the subject (S4 in FIG. 7 and a waveform w4 in FIG. 6).

After a predetermined time elapses from the start of the exposure, the first driving circuit 21 turns off the electronic shutter of the image sensor 22 to end the exposure of fluorescence emission from the subject (S5 in FIG. 7 and a timing t3 in FIG. 6).

Simultaneously with the exposure end, the image processor 35 starts reading of an IR fluorescence signal from the image sensor 22 (S6 in FIG. 7 and a timing t3 and a waveform w6 in FIG. 6). The IR fluorescence signal is a signal obtained by the exposure of the fluorescence emission. The reading of the IR fluorescence signal ends after a reading time corresponding to the number of pixels elapses (a timing t4 in FIG. 6).

When the reading of the IR fluorescence signal by the image processor 35 ends (a time t4 in FIG. 6), the display processor 36 outputs a display signal of a fluorescence emission light image obtained from the IR fluorescence signal to the monitor 40. The monitor 40 displays the fluorescence emission light image during a period Ti until the fluorescence emission light image is switched to the visible light image (a waveform w8 in FIG. 6).

Further, when the reading of the IR fluorescence signal by the image processor 35 ends (a timing t4 in FIG. 6), the controller 31 drives the second driving circuit 32 in order to cause the visible light to be emitted. The second driving circuit 32 turns on the visible light source 34 to cause the visible light to be emitted (S7 in FIG. 7, and a timing t4 and a waveform w3 in FIG. 6).

When the visible light source 34 is turned on and emits the visible light, the visible light is radiated from the irradiation windows 28z and 28y to the subject through the optical fiber 28 in the scope 13, and illuminates a part of the periphery including the affected part. When the visible light reflected by the affected part or the like passes through the imaging window 12z, the visible light is condensed by the lens 24, transmitted through the IR excitation light cut filter 23, and formed as an image on the imaging surface of the image sensor 22.

Further, when the reading of the IR fluorescence signal by the image processor 35 ends (a time t4 in FIG. 6), the first driving circuit 21 outputs the sensor reset signal to the image sensor 22 to return the image sensor 22 to a state before the start of the exposure (S8 in FIG. 7).

After the sensor is reset, the first driving circuit 21 turns on the electronic shutter of the image sensor 22 to start exposure by the visible light (S9 in FIG. 7).

After a predetermined time elapses from the start of the exposure, the first driving circuit 21 turns off the electronic shutter of the image sensor 22 to end the exposure of the visible light (S10 in FIG. 7 and a timing t5 in FIG. 6).

Simultaneously with the visible light exposure ending, the image processor 35 starts reading of a visible light signal from the image sensor 22 (S11 in FIG. 7 and a waveform w7 in FIG. 6). The visible light signal is a signal obtained by the exposure of the visible light. The reading of the visible signal ends after a reading time corresponding to the number of pixels elapses (a timing t6 in FIG. 6).

When the reading of the visible light signal by the image processor 35 ends, the display processor 36 outputs a display signal of a visible signal image obtained from the visible light signal to the monitor 40. The monitor 40 displays the visible light image during a period Tr until the visible light image is switched to the fluorescence emission light image (a waveform w8 in FIG. 6).

Further, when the exposure of the visible light ends at a timing t5 in FIG. 6, the second driving circuit 32 turns off the visible light source 34 to cause the visible light not to be emitted (S12 in FIG. 7 and a waveform w3 in FIG. 6).

Thereafter, the controller 31 determines whether to end the imaging (S13). The end of the imaging is determined, for example, according to whether the user performs an operation to turn off a switch (not illustrated) provided in the video processor 30 or the endoscope 10 and this operation is received by the endoscope system 5. In a case in which the imaging does not end, the process returns to S3 in FIG. 7. As described above, the first driving circuit 21 outputs the sensor reset signal to the image sensor 22 to return the image sensor 22 to the state before the start of the exposure (S3 in FIG. 7 and a timing t5 of FIG. 6).

By contrast, when the imaging ends in S13, the controller 31 outputs a signal for ending the photoelectric conversion of the image sensor 22 to the first driving circuit 21 (S14 in FIG. 7). The second driving circuit 32 turns off the IR excitation light source 33 to cause the IR excitation light not to be emitted (S15 in FIG. 7). The imaging operation in a case in which continuous irradiation with the IR excitation light is performed, which is illustrated in FIG. 7, ends.

Thus, in the endoscope system 5, the imaging operation is performed during the imaging period. During this period, the fluorescence emission light image and the visible light image are displayed in the same area of the monitor 40.

Since the switching between the displays of the fluorescence emission light image and the visible light image indicated by the waveform w8 in FIG. 6 is performed in a short period of time, it can be said that the fluorescence emission light image and the visible light image are displayed to overlap. Further, although the example in which the imaging operation (imaging period) starts or ends according to the on or off operation of the switch has been described herein, the imaging operation (imaging period) may start or end through any other method (for example, detection of a predetermined time using a timer).

Figure 8:
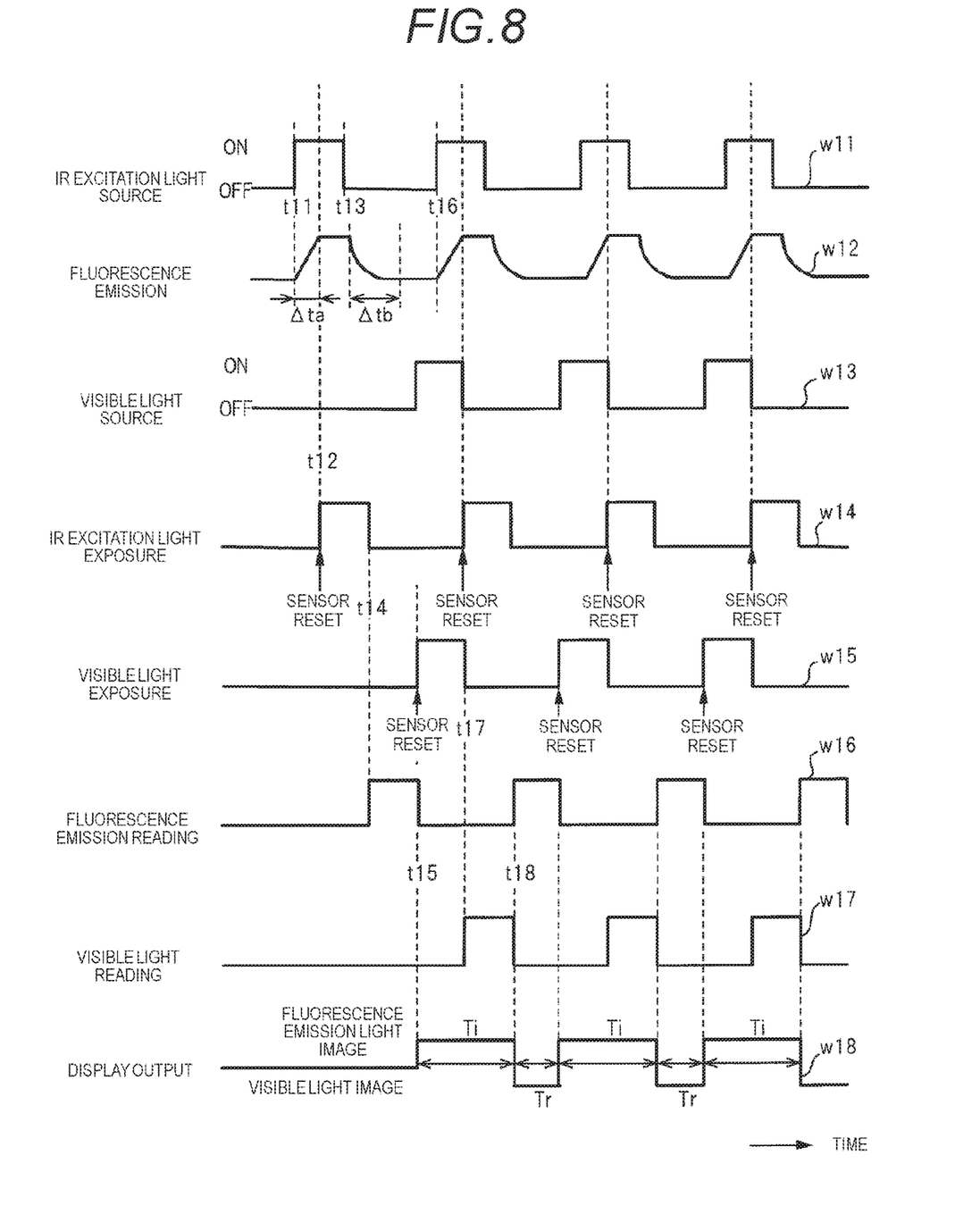
FIG. 8 is a timing chart diagram illustrating an example of an imaging operation of the endoscope system 5 in a case in which pulse irradiation with IR excitation light is performed.
Figure 9:
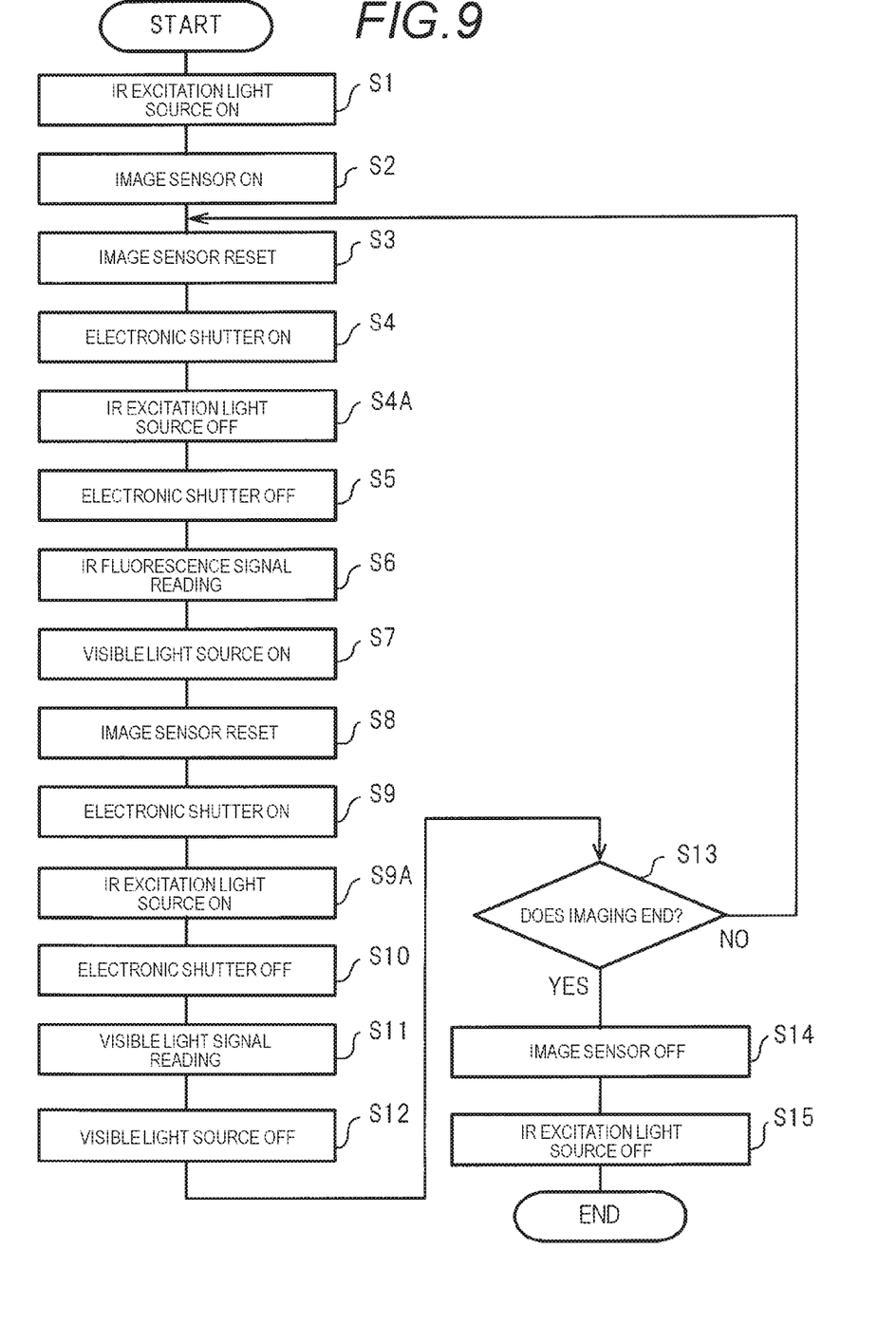
FIG. 9 is a flowchart illustrating an example of an imaging operation procedure of the endoscope system 5 in a case in which pulse irradiation with IR excitation light is performed.

FIG. 8 is a timing chart diagram illustrating an imaging operation of the endoscope system 5 in a case in which pulse irradiation with the IR excitation light is performed. FIG. 9 is a flowchart illustrating an imaging operation procedure of the endoscope system 5 in a case in which pulse irradiation with the IR excitation light is performed. In FIGS. 8 and 9, the same processes as those in FIGS. 6 and 7 are denoted with the same step signs and a description thereof will be omitted or simplified.

The endoscope system 5 starts an imaging operation, for example, by receiving an operation of turning ON a switch (not illustrated) provided in the video processor 30 or the endoscope 10, similar to the cases of FIGS. 6 and 7.

When an imaging operation is started, the controller 31 drives the second driving circuit 32. The second driving circuit 32 turns ON the IR excitation light source 33 to cause the IR excitation light to be emitted (S1 in FIG. 9 and a timing t11 in FIG. 8).

When the IR excitation light source 33 emits the IR excitation light, the IR excitation light is radiated from the irradiation window 27z to the subject through the optical fiber 27 in the scope 13, and illuminates a part of the periphery including the affected part. When light from the subject such as the affected part passes through the imaging window 12z, the light is condensed by the lens 24. In the light from the subject such as the affected part, the IR excitation light reflected by the subject is blocked by the IR excitation light cut filter 23, whereas fluorescence emission light from the subject is transmitted through the IR excitation light cut filter 23 to form an image on the imaging surface of the image sensor 22.

In FIGS. 8 and 9, the IR excitation light source 33 is switched on or off in the imaging period. Therefore, the IR excitation light is radiated as a certain amount of a pulse light (waveform w11 in FIG. 8).

The subject (affected part) pulse-irradiated with the IR excitation light emits fluorescence emission light, and the fluorescence emission light is output (a waveform w12 in FIG. 8). This fluorescence emission light reaches a peak light amount with a delay by a predetermined time $\Delta ta$ (for example, several msec) from the pulse irradiation of IR excitation light, and the peak light amount is temporarily maintained and then reduced over a predetermined period of time $\Delta tb$. Here, after the fluorescence emission light output from the subject reaches a predetermined amount or more (here, peak light amount), the irradiation of the IR excitation light is started by the predetermined time $\Delta ta$ before the start of the exposure so that the exposure of the fluorescence emission is started.

The controller 31 outputs a signal for starting the photoelectric conversion of the image sensor 22 to the first driving circuit 21 (image sensor ON) (S2 in FIG. 9). When the first driving circuit 21 receives this signal, the first driving circuit 21 outputs a sensor reset signal to the image sensor 22 to return the image sensor 22 to a state before the start of exposure (S3 in FIG. 9, and a timing t12 in FIG. 8). At this timing t12, the fluorescence emission light from the subject reaches the peak light amount.

After the sensor is reset, the first driving circuit 21 turns on the electronic shutter of the image sensor 22 to start the exposure of the fluorescence emission from the subject (S4 in FIG. 9 and a waveform w14 in FIG. 8).

After a time corresponding to a pulse width elapses since the second driving circuit 32 has turned on the IR excitation light source 33 to cause the IR excitation light to be emitted, the second driving circuit 32 turns off the IR excitation light source 33 to cause the IR excitation light not to be emitted (S4A in FIG. 9 and a timing t13 in FIG. 8). After the time corresponding to the pulse width elapses corresponds to after a predetermined time elapses from the start of the exposure of the fluorescence emission.

After a predetermined time elapses from the start of the exposure of the fluorescence emission, the first driving circuit 21 turns off the electronic shutter of the image sensor 22 to end the exposure of fluorescence emission from the subject (S5 in FIG. 9 and a timing t14 in FIG. 8).

Simultaneously with the exposure end, the image processor 35 starts reading of an IR fluorescence signal from the image sensor 22 (S9 in FIG. 7 and a waveform w16). The reading of the IR fluorescence signal ends after a reading time corresponding to the number of pixels elapses (a timing t15 in FIG. 8).

When the reading of the IR fluorescence signal by the image processor 35 ends, the display processor 36 outputs a display signal of a fluorescence emission light image obtained from the IR fluorescence signal to the monitor 40. The monitor 40 displays the fluorescence emission light image on a screen during a period Ti until the fluorescence emission light image is switched to the visible light image (a waveform w18 in FIG. 8).

Further, when the reading of the IR fluorescence signal by the image processor 35 ends (a timing t15 in FIG. 8), the controller 31 drives the second driving circuit 32 in order to cause the visible light to be emitted. The second driving circuit 32 turns on the visible light source 34 to cause the visible light to be emitted (S7 in FIG. 9, and a timing t15 and a waveform w13 in FIG. 8).

When the visible light source 34 is turned on and emits the visible light, the visible light is radiated from the irradiation windows 28z and 28y to the subject through the optical fiber 28 in the scope 13, and illuminates a part of the periphery including the affected part. When the light reflected by the affected part or the like passes through the imaging window 12z, the visible light is condensed by the lens 24, transmitted through the IR excitation light cut filter 23, and formed as an image on the imaging surface of the image sensor 22.

Further, when the reading of the IR fluorescence signal by the image processor 35 ends (a time t15 in FIG. 8), the first driving circuit 21 outputs the sensor reset signal to the image sensor 22 to return the image sensor 22 to a state before the start of the exposure (S8 in FIG. 9).

After the sensor is reset, the first driving circuit 21 turns on the electronic shutter of the image sensor 22 to start exposure by the visible light (S9 in FIG. 9).

After the exposure by the visible light starts, the second driving circuit 32 turns on the IR excitation light source 33 to cause the IR excitation light to be emitted before a predetermined time $\Delta ta$ from the next start of the exposure by the IR excitation light (S9A in FIG. 9 and a timing t16 in FIG. 8).

After a predetermined time elapses from the start of the exposure by the visible light, the first driving circuit 21 turns off the electronic shutter of the image sensor 22 to end the exposure by the visible light (S10 in FIG. 9 and a timing t17 in FIG. 8).

Simultaneously with the visible light exposure ending, the image processor 35 starts reading of a visible light signal from the image sensor 22 (S11 in FIG. 9 and a waveform w17 in FIG. 8). The reading of the visible light signal ends after a reading time corresponding to the number of pixels elapses (a timing t18 in FIG. 8).

When the reading of the visible light signal by the image processor 35 ends, the display processor 36 outputs a display signal of a visible signal image obtained from the visible light signal to the monitor 40. The monitor 40 displays the visible light image on a screen during a period Tr until the visible light image is switched to the fluorescence emission light image (a waveform w18 in FIG. 8).

Simultaneously with the end of the exposure of the visible light, the second driving circuit 32 turns off the visible light source 34 to cause the visible light not to be emitted (S12 in FIG. 9 and a waveform w13 in FIG. 8).

Thereafter, the controller 31 determines whether to end the imaging or not (S13). The end of the imaging is determined, for example, according to whether the user performs an operation to turn off a switch (not illustrated) provided in the video processor 30 or the endoscope 10 and this operation is received by the endoscope system 5. In a case in which the imaging does not end, the process returns to S3 in FIG. 9. As described above, the first driving circuit 21 outputs the sensor reset signal to the image sensor 22 to return the image sensor 22 to the state before the start of the exposure (S3 in FIG. 9 and a timing t17 of FIG. 8).

By contrast, when the imaging ends in S13, the controller 31 outputs a signal for ending the photoelectric conversion of the image sensor 22 to the first driving circuit 21 (S14 in FIG. 9). The second driving circuit 32 turns off the IR excitation light source 33 to cause the IR excitation light not to be emitted (S15 in FIG. 9). The imaging operation in a case in which pulse irradiation with the IR excitation light is performed, which is illustrated in FIG. 9, ends.

Thus, the imaging operation is performed during the imaging period. During this period, the fluorescence emission light image and the visible light image are displayed in the same area of the monitor 40.

Since the switching between the displays of the fluorescence emission light image and the visible light image indicated by the waveform w18 in FIG. 8 is performed in a short period of time, it can be said that the fluorescence emission light image and the visible light image are displayed to overlap. Further, although the example in which the imaging operation (imaging period) starts or ends according to the on or off operation of the switch has been described herein, the imaging operation (imaging period) may start or end through any other method (for example, detection of a predetermined time using a timer).

[Effects]

Thus, the endoscope system 5 includes the visible light source 34, the IR excitation light source 33, the second driving circuit 32, and the image sensor 22. In the imaging operation, the IR excitation light source 33 starts the emission of the IR excitation light by a predetermined time $\Delta t$ before the start of photoelectric conversion of the fluorescence emission light due to driving of the second driving circuit 32. The image sensor 22 generates the visible light image including the subject through photoelectric conversion of the visible light. The image sensor 22 generates the fluorescence emission light image including the subject that emits fluorescence emission light due to excitation by the IR excitation light, through photoelectric conversion of the fluorescence emission light. The monitor 40 alternately switches between and outputs (displays) the visible light image and the fluorescence emission light image.

The visible light source 34 is an example of a first light source. The IR excitation light source 33 is an example of a second light source. The second driving circuit 32 is an example of a driving circuit. The monitor 40 is an example of an output device. The photoelectric conversion of the visible light is an example of first photoelectric conversion. The photoelectric conversion of the fluorescence emission light is an example of second photoelectric conversion. The IR excitation light is an example of non-visible light. The visible light image is an example of a first image. The fluorescence emission light image is an example of a second image.

Accordingly, the endoscope system 5 starts the emission of the IR excitation light by the predetermined time $\Delta t$ before the start of the photoelectric conversion of the fluorescence emission light caused by IR excitation light. Therefore, the endoscope system 5 can receive the fluorescence emission light according to the delay of the fluorescence emission light and correspondingly can increase the received light amount of fluorescence emission light. Therefore, the endoscope system 5 can prevent a reduction in image quality of the fluorescence emission light image.

Further, the IR excitation light source 33 may continue to emit light in the imaging period in which the visible light image and the fluorescence emission light image are captured, due to driving of the second driving circuit 32.

Accordingly, after the fluorescence emission light reaches a predetermined amount or more (for example, a peak light amount), the fluorescence emission does not reach the peak light later than the IR excitation light, and a sufficient amount of the fluorescence emission light is always obtained. Therefore, the endoscope system 5 may not have to wait for an increase (rise) in the light amount of fluorescence emission light. As the endoscope system 5 does not have to wait for the increase in the light amount of fluorescence emission light, the endoscope system 5 can increase a frame rate when alternately displaying the fluorescence emission light image and the visible light image. Therefore, with the endoscope system 5, if the frame rate increases, for example, flickering can be reduced and the image quality can be improved when the fluorescence emission light image and the visible light image are displayed to overlap on the monitor 40.

Further, the predetermined time $\Delta t$ may be a time determined based on a difference between the timing t1 at which the emission of the IR excitation light starts and a timing t1+$\Delta t$ at which the light amount of the fluorescence emission light reaches the predetermined amount or more (here, peak light amount). The timing t1 is an example of a first time point. The timing t1+$\Delta t$ is an example of a second time point.

Accordingly, the endoscope system 5 can start the exposure after the light amount of fluorescence emission light is equal to or larger than a predetermined amount (for example, the peak light amount), and can sufficiently secure the received light amount of the fluorescence emission light. Therefore, the endoscope system 5 can achieve high definition of the fluorescence emission light image. The predetermined amount is not limited to the peak light amount, and can be set to any value such as ⅔ of the peak light amount.

Further, the monitor 40 may display the visible light image and the fluorescence emission light image on a common area of the monitor 40.

Accordingly, in a case in which the frame rate (switching speed) is equal to or greater than a predetermined value, the user can reduce a sense of flickering due to an afterimage effect and can view an image in which the visible light image and the fluorescence emission light image overlap. Further, since a position of the observation part (for example, an internal organ of a human body) may be shifted over time, the user can easily recognize a correspondence relationship between positions of the two images, unlike a case in which the visible light image and the fluorescence emission light image are separately captured.

Further, the IR excitation light cut filter 23 may block an optical component in a frequency bandwidth including a frequency of the IR excitation light reflected by the subject, and transmit an optical component in a frequency bandwidth including frequencies of the fluorescence emission light and the visible light.

Accordingly, the endoscope system 5 can achieve high definition of the fluorescence emission light image as the IR excitation light is blocked. Further, the IR excitation light cut filter 23 transmits the visible light. Accordingly, the image sensor 22 can capture an optical image by the visible light.

Further, the image processor 35 may control a gain of at least one of the fluorescence emission light image and the visible light image. The image processor 35 is one example of a gain controller.

Accordingly, it is possible to adjust luminance of the fluorescence emission light image and luminance of the visible light image to the same extent. Through the gain adjustment, the user can reduce a sense of a difference in luminance between the fluorescence emission light image and the visible light image displayed on the monitor 40.

Further, the visible light source 34 and IR excitation light source 33 may alternately emit the light due to driving of the second driving circuit 32. In a case in which the second driving circuit 32 causes the IR excitation light and the visible light to be alternately emitted, the second driving circuit 32 causes the IR excitation light to be emitted, for example, early by a predetermined time Δta until the fluorescence emission by the IR excitation light reaches the peak light amount.

Accordingly, the endoscope system 5 can receive the fluorescence emission light according to the delay of the fluorescence emission and can correspondingly increase the received light amount of the fluorescence emission light. Therefore, even in a case in which the endoscope system 5 causes the IR excitation light source 33 to perform a switching operation so that the IR excitation light is pulse-emitted, the endoscope system 5 can maintain the amount of light so that the received light amount increases, and reduce degradation of the image quality of the fluorescence emission light image. In the endoscope system 5, it is possible to reduce heat generation in the IR excitation light source 33 by reducing power consumption, leading to a longer lifespan of the IR excitation light source 33, unlike a case in which the IR excitation light is caused to be continuously emitted.

Further, in the light source control method in the endoscope system 5, the endoscope system 5 emits the visible light to the subject, and generates a visible light image including the subject through photoelectric conversion of the visible light. Further, in this method, the endoscope system 5 emits the excitation light to the subject, and generates the fluorescence emission light image including the subject that emits fluorescence emission light through photoelectric conversion of the fluorescence emission light. Further, in this method, the endoscope system 5 alternately switches and outputs the visible light image and the fluorescence emission light image, and starts the emission of the IR excitation light by a predetermined time Δt before the start of photoelectric conversion of the fluorescence emission light.

Accordingly, the endoscope system 5 starts the emission of the IR excitation light by the predetermined time Δt before the start of the photoelectric conversion of the fluorescence emission light caused by IR excitation light. Therefore, the endoscope system 5 can receive the fluorescence emission light according to the delay of the fluorescence emission light and can correspondingly increase the received light amount of fluorescence emission light. Therefore, the endoscope system 5 can prevent a reduction in image quality of the fluorescence emission light image.

(Other Embodiments)

As described above, the first embodiment has been described as an illustration of the technology in this disclosure. However, the technology in the present disclosure is not limited thereto and can be applied to embodiments in which changes, substitutions, additions, omissions, or the like are performed.

Although the example in which the visible light source 34 emits pulse light has been described in the first embodiment, the visible light source 34 may continuously emit light in the imaging period. Driving of the visible light source 34 is controlled by the second driving circuit 32.

Although the irradiation timings of the visible light and the IR excitation light have been shifted from each other in the first embodiment, the irradiation timings of the visible light and the IR excitation light may partially overlap.

Although the example in which one image sensor (single-plate camera) capable of imaging the IR light and the RGB light (visible light) is used has been described in the first embodiment, another type of camera may be used. The other type of camera includes, for example, two image sensors (2-plate camera) including an IR image sensor and a RGB image sensor.

Although the example in which the ICG is administered as an optical imaging agent into a living body has been described in the first embodiment, an optical imaging agent other than the ICG may be administered. In this case, spectral characteristics in a wavelength region of non-visible light may be determined according to a wavelength of the excitation light for exciting the optical imaging agent. Therefore, the IR excitation light cut filter 23 may have characteristics other than the characteristics illustrated in FIG. 5.

Although a chemical that emits fluorescence emission light in a wavelength region of infrared light is used in the first embodiment, a chemical that emits the fluorescence emission light in a wavelength region of ultraviolet light may be used. Even in a case in which the ultraviolet light is used, the endoscope 10 can capture an image of the affected part that emits the fluorescence emission light, similar to a case in which an optical imaging agent that emits the fluorescence emission light in a near infrared region is used.

In the first embodiment, the monitor 40 capable of displaying the fluorescence emission light image and the visible light image on the screen has been shown as the output device, but the present invention is not limited thereto. For example, the output device may be a printer capable of printing the fluorescence emission light image and the visible light image or a signal output device capable of outputting an image signal of each of the fluorescence emission light image and the visible light image. Further, the output device may be, for example, a storage device capable of storing the image data of each of the fluorescence emission light image and the visible light image in a recording medium, or a communication device capable of communicating the image data of each of the fluorescence emission light image and the visible light image.

In the first embodiment, the video processor 30, the controller 31, the image processor 35, and the display processor 36 may be physically configured using any method. However, if a programmable controller or processor is used, processing content can be changed through a change in the program, and accordingly, it is possible to increase the degree of freedom in designing. Further, the controller or the processor may be configured of one semiconductor chip or may be physically configured of a plurality of semiconductor chips. When the controller or the processor is configured of a plurality of semiconductor chips, each control in the first embodiment may be realized by separate semiconductor chips. In this case, it can be considered that one controller or processor is configured of the plurality of semiconductor chips. Further, the controller or processor may be configured of a member (for example, a capacitor) having a function different from a semiconductor chip. Further, one semiconductor chip may be configured so as to realize a function of the controller or processor and other functions.

Although the hardware configuration of the endoscope system 5 has been illustrated in FIG. 4 in the first embodiment, at least a portion of the hardware configuration may be realized by software.

What is claimed is:

1. An endoscope system comprising:
    a first light source that emits visible light to a subject;
    a second light source that emits non-visible light to the subject;
    a driving circuit that drives the first light source and the second light source;
    an image sensor that generates a first image including the subject through first photoelectric conversion using the visible light, and generates a second image including the subject, that emits fluorescence emission light due to excitation by the non-visible light, through second photoelectric conversion using the fluorescence emission light;
    an output device that alternately switches between and outputs the first image and the second image; and
    a gain controller that controls a gain of the first image while the second light source emits non-visible light and increases a gain of the second image while the second light source emits non-visible light, wherein
    the second light source starts non-visible light emission a predetermined time before a start of the second photoelectric conversion and continues to emit non-visible light during a period in which the first light source emits visible light to a subject, and
    the predetermined time is determined based on a difference between a first point in time at which emission of the non-visible light starts and a second point in time at which an amount of the fluorescence emission excited by the non-visible light emitted at the first point in time becomes equal to or greater than a predetermined amount.

2. The endoscope system according to claim 1, wherein the second light source continues to emit non-visible light in an imaging period in which the first image and the second image are captured, due to driving of the driving circuit.

3. The endoscope system according to claim 1, further comprising:
    a filter arranged on a light reception side of the image sensor to block an optical component in a predetermined frequency bandwidth including a frequency of the non-visible light emitted by the second light source and transmit an optical component in a predetermined frequency bandwidth including a frequency of the fluorescence emission light and the visible light.

4. A light source control method in an endoscope system, the method comprising:
    emitting visible light to a subject;
    generating a first image including the subject through first photoelectric conversion using the visible light;
    emitting non-visible light to the subject;
    generating a second image including the subject, the subject emitting fluorescence emission light due to excitation by the non-visible light, through second photoelectric conversion using the fluorescence emission light;
    alternately switching between and outputting the first image and the second image; and
    controlling a gain of the first image while the second light source emits non-visible light and increasing a gain of the second image while the second light source emits non-visible light, wherein,
    the emitting non-visible light starting a predetermined time before start of the second photoelectric conversion and continuing in a period in which the emitting visible light to a subject occurs, and
    the predetermined time based on a difference between a first point in time at which emission of the non-visible light starts and a second point in time at which an amount of the fluorescence emission excited by the non-visible light emitted at the first point in time becomes equal to or greater than a predetermined amount.

5. The light source control method according to claim 4, further comprising:
    blocking an optical component in a predetermined frequency bandwidth including a frequency of the emitted non-visible light and transmitting an optical component in a predetermined frequency bandwidth including a frequency of the fluorescence emission light and the visible light.

6. The light source control method according to claim 4, further comprising:
    the emitting non-visible light continuing in an imaging period in which the first image and the second image are captured.

7. The light source control method according to claim 4, wherein the controlling the gain of the first image and increasing the a gain of the second image further comprises controlling the gain of the first image independent of increasing the gain of the second image.

8. The endoscope system of claim 1, wherein the gain controller controls the gain of the first image independent of increasing the gain of the second image.

9. The endoscope system of claim 1, wherein the gain controller that controls a gain of the first image, controls the gain of the first image by decreasing the gain of the first image.

10. The endoscope system of claim 1, wherein the gain controller that controls a gain of the first image, controls the gain of the first image by increasing the gain of the first image and increases the gain of the second image to be higher than the gain of the first image.

11. The light source control method of claim 4, wherein the controlling the gain of the first image comprises decreasing the gain of the first image.

12. The light source control method of claim 4, wherein controlling the gain of the first image comprises increasing the gain of the first image and increasing the gain of the second image comprises increasing the gain of the second to be higher than the gain of the first image.

13. An endoscope system comprising:
    a first light source that emits visible light to a subject;
    a second light source that emits non-visible light to the subject;
    a driving circuit that drives the first light source and the second light source;
    an image sensor that generates a first image including the subject through first photoelectric conversion using the visible light, and generates a second image including the subject, that emits fluorescence emission light due to excitation by the non-visible light, through second photoelectric conversion using the fluorescence emission light;

an output device that alternately switches between and outputs the first image and the second image; and a gain controller that decreases a gain of the first image while the second light source emits non-visible light and controls a gain of the second image while the second light source emits non-visible light, wherein the second light source starts non-visible light emission a predetermined time before a start of the second photoelectric conversion and continues to emit non-visible light during a period in which the first light source emits visible light to a subject, and the predetermined time is determined based on a difference between a first point in time at which emission of the non-visible light starts and a second point in time at which an amount of the fluorescence emission excited by the non-visible light emitted at the first point in time becomes equal to or greater than a predetermined amount.

14. The endoscope system according to claim 13, wherein the second light source continues to emit non-visible light in an imaging period in which the first image and the second image are captured, due to driving of the driving circuit.

15. The endoscope system according to claim 13, further comprising:

a filter arranged on a light reception side of the image sensor to block an optical component in a predetermined frequency bandwidth including a frequency of the non-visible light emitted by the second light source and transmit an optical component in a predetermined frequency bandwidth including a frequency of the fluorescence emission light and the visible light.

16. A light source control method in an endoscope system, the method comprising:

emitting visible light to a subject;

generating a first image including the subject through first photoelectric conversion using the visible light;

emitting non-visible light to the subject;

generating a second image including the subject, the subject emitting fluorescence emission light due to excitation by the non-visible light, through second photoelectric conversion using the fluorescence emission light;

alternately switching between and outputting the first image and the second image; and decreasing a gain of the first image while the second light source emits non-visible light and controlling a gain of the second image while the second light source emits non-visible light, wherein, the emitting non-visible light starting a predetermined time before start of the second photoelectric conversion and continuing in a period in which the emitting visible light to a subject occurs, and the predetermined time based on a difference between a first point in time at which emission of the non-visible light starts and a second point in time at which an amount of the fluorescence emission excited by the non-visible light emitted at the first point in time becomes equal to or greater than a predetermined amount.

17. The light source control method according to claim 16 further comprising:

the emitting non-visible light continuing in an imaging period in which the first image and the second image are captured.

18. The light source control method according to claim 16, further comprising:

blocking an optical component in a predetermined frequency bandwidth including a frequency of the emitted non-visible light and transmitting an optical component in a predetermined frequency bandwidth including a frequency of the fluorescence emission light and the visible light.

* * * * *